United States Patent [19]

Heffernan et al.

[11] Patent Number: 5,620,425
[45] Date of Patent: Apr. 15, 1997

[54] METHOD FOR THE PREPARATION OF PRE-FILLED PLASTIC SYRINGES

[75] Inventors: Gayle Heffernan, Middlesex; Allen Welsher, East Brunswick, both of N.J.

[73] Assignee: Bracco International B.V., Amsterdam, Netherlands

[21] Appl. No.: 147,353

[22] Filed: Nov. 3, 1993

[51] Int. Cl.$^6$ ..................................................... A61M 1/00
[52] U.S. Cl. ......................... 604/281; 604/187; 604/232; 141/11; 128/898
[58] Field of Search .................................. 604/187, 265, 604/240, 243, 244, 201, 202, 232, 238, 272, 28; 128/898; 422/25–28; 141/5, 11; 264/250

[56] References Cited

U.S. PATENT DOCUMENTS

| | | |
|---|---|---|
| 2,546,385 | 3/1951 | Christina . |
| 2,671,742 | 3/1954 | Cozzoli . |
| 2,883,262 | 4/1959 | Borin ..................................... 422/26 X |
| 3,404,946 | 10/1968 | Reis . |
| 3,421,840 | 1/1969 | Pechmann ............................. 141/11 X |
| 3,746,022 | 7/1973 | Fillion et al. . |

(List continued on next page.)

FOREIGN PATENT DOCUMENTS

| | | |
|---|---|---|
| 555900 | 8/1983 | European Pat. Off. . |
| 61-296845 | 5/1994 | Japan . |

OTHER PUBLICATIONS

European Plastic News, vol. 18, No. 8, Oct. 1991, pp. 24–25; Cooke F. "Getting started in medical plastics".

Antec 91—Conference Proceedings, May 1991, pp. 412–416; Galic G. et al., "Molded parts discharged without opening the mold".

Database Rapra, Rapra Technology Ltd., Shawbury, Shrewsbury, Shropshire, Great Britain, An: 489025; Kirkland C., "Safer syringes boost moulder opportunities".

Kunststoffe, vol. 81, No. 9, Sep. 1991, München, pp. 768–770; Eckardt H., "Spritzqiessen im Reinraum".

*Disposable Syringes: Klockner Standards for Mass Production*, Plastics Southern Africa, vol. 21, No. 4, p. 10 Sep. 1991.

Uotila et al., "New Concepts in the Manufacturing and Sterilization of LVP's in Plastic Bottles", Journal of Parenteral Science and Technology, vol. 35, No. 4, Jul.–Aug. 1981, pp. 170–175.

Schuck, "Steam Sterilization of Solutions in Plastic Bottles", International Symposium on Sterilization and Sterility Testing of Biological Substances, Madrid, 1973, Develop. biol. Standard, vol. 23, pp. 1–5 (Karger, Basel/München/Paris/London/New York/Sydney 1974).

Ruig, "The 'Pharma Hydromatic' Hydrostatic Continuous Steriliser for Sterilising Infusion Liquids in Glass Bottles and Plastic Containers", Pharma Int., pp. 9–14 (5) 1972.

Portnoff et al., "The Processing of Small Volume Parenterals and Related Sterile Products", Pharmaceutical Dosage Forms: Parenteral Medications, vol. 1, 1984, pp. 203, 220–227 and 229.

Sharp, "Manufacture of Sterile Pharmaceutical Products Using 'blow–fill–seal' Technology", The Pharmaceutical Journal, Jul. 25, 1987, pp. 106–108.

(List continued on next page.)

*Primary Examiner*—Corrine M. McDermott
*Assistant Examiner*—V. Alexander
*Attorney, Agent, or Firm*—George P. Hoare, Jr.; Rogers & Wells

[57] ABSTRACT

A novel method for the preparation of a pre-filled plastic syringe, and preferably the preparation of a plastic syringe pre-filled with a diagnostic contrast agent, wherein said syringe comprises as components a barrel, a tip seal capable of sealing the nozzle of the barrel and a piston capable of sliding in the barrel and sealing the open end of the barrel opposite the nozzle, comprising the steps of (a) providing at least one component of said syringe which is molded under conditions which are substantially free of pyrogens and viable and non-viable particulates; and (b) filling and assembling said syringe.

16 Claims, 3 Drawing Sheets

U.S. PATENT DOCUMENTS

| | | |
|---|---|---|
| 4,130,117 | 12/1978 | Van Eck . |
| 4,196,732 | 4/1980 | Wardlaw et al. . |
| 4,243,080 | 1/1981 | Choksi et al. . |
| 4,317,446 | 3/1982 | Ambrosio et al. . |
| 4,342,184 | 8/1982 | Van Eck et al. . |
| 4,434,820 | 3/1984 | Glass . |
| 4,474,734 | 10/1984 | Cooper ........................................ 422/34 |
| 4,475,903 | 10/1984 | Steenhuisen et al. . |
| 4,557,898 | 12/1985 | Greene et al. ............................ 422/28 |
| 4,568,336 | 2/1986 | Cooper . |
| 4,628,969 | 12/1986 | Jurgens, Jr. et al. ........................ 141/1 |
| 4,703,781 | 11/1987 | Meyer et al. . |
| 4,715,854 | 12/1987 | Vaillancourt . |
| 4,718,463 | 1/1988 | Jurgens et al. . |
| 4,747,829 | 5/1988 | Jacob et al. . |
| 4,758,230 | 7/1988 | Rycroft . |
| 5,067,948 | 11/1991 | Haber et al. . |
| 5,077,008 | 12/1991 | Kralovic et al. ........................... 422/37 |
| 5,207,983 | 5/1993 | Liebert et al. . |
| 5,242,400 | 9/1993 | Blake et al. . |
| 5,412,068 | 5/1995 | Tang et al. ............................... 528/370 |
| 5,439,643 | 8/1995 | Liebert ....................................... 422/25 |
| 5,478,324 | 12/1995 | Meyer ....................................... 604/203 |

OTHER PUBLICATIONS

The Parenteral Drug Association, "Comments on FDA's Guideline on Sterile Drug Products Produced by Aseptic Processing", Pharmaceutical Manufacturing, Nov. 1985, pp. 24–29.

Solomon et al., "Plastic Containers for Parenterals", Pharmaceutical Dosage Forms, vol. 2, 1986, pp. 111 and 140–142.

Sharp, "Aseptic Validation of a Form/Fill/Seal Installation: Principles and Practice", Journal of Parenteral Science & Technology, vol. 44, No. 5, Sep.–Oct. 1990, pp. 289–292.

Pharmacopeial Forum, In–Process Revision, vol. 18, No. 5, Sep.–Oct., 1992, pp. 4048–4054.

Federal Standard 209E, Airborne Particulate Cleanliness Classes in Cleanrooms and Clean Zones, Sep. 11, 1992, pp. 1–48.

| Class Name | Class limits | | | | | | | | |
|---|---|---|---|---|---|---|---|---|---|
| | 0.1 μm | Volume units - (ft³) | 0.2 μm | Volume units - (ft³) | 0.3 μm | Volume units - (ft³) | 0.5 μm | Volume units - (ft³) | 5 μm | Volume units - (ft³) |
| 100 | | --- | | 750 | | 300 | | 100 | | --- |
| 1,000 | | --- | | --- | | --- | | 1000 | | 7.00 |
| 10,000 | | --- | | --- | | --- | | 10,000 | | 70.0 |
| 100,000 | | --- | | --- | | --- | | 100,000 | | 700 |

FIG. 2

| Class | cfu per cubic foot of air | cfu per cubic meter** |
|---|---|---|
| MCB-1 | Less than 0.03 | Less than 1 |
| MCB-2 | Less than 0.5 | Less than 18 |
| MCB-3 | Less than 2.5 | Less than 88 |

FIG. 3A

| Class | per 30 cm$^2$ |
|---|---|
| MCB-1 | 3 |
| MCB-2 | 5 |
| | 10 (floor) |

FIG. 3B

| Class | Gloves | Mask/Boots/Gown |
|---|---|---|
| MCB-1 | 3 | 5 |
| MCB-2 | 5 | 10 |

FIG. 3C

METHOD FOR THE PREPARATION OF PRE-FILLED PLASTIC SYRINGES

FIELD OF THE INVENTION

The present invention relates to a novel method for the preparation of pre-filled plastic syringes, and preferably to the preparation of plastic syringes pre-filled with diagnostic contrast agents.

BACKGROUND OF THE INVENTION

Plastic syringes, pre-filled with liquid or semi-solid materials suitable for diagnosis and/or treatment of medical conditions, find utility in the pharmaceutical arts. As can readily be appreciated, it is desirable that such syringes are sterile and contain minimal amounts of pyrogens and viable and non-viable particulates.

Methods for preparing pre-filled plastic syringes have previously been disclosed. For example, U.S. Pat. No. 4,718,463 describes a method for the preparation of pre-filled plastic syringes comprising, among other steps, a step wherein the barrel of the syringe is washed with a multiplicity of jets of water to remove debris and pyrogens from the barrel, followed by assembly and filling of the syringe and a terminal autoclaving step wherein the filled syringe and its contents are sterilized.

SUMMARY OF THE INVENTION

The present invention provides a method for the preparation of a pre-filled plastic syringe, comprising the steps of:

(a) providing at least one component of said syringe which is molded under conditions which are substantially free of pyrogens and viable and non-viable particulates; and (b) filling and assembling said syringe. Preferably, the syringe comprises as components a barrel, a tip seal capable of sealing the nozzle of the barrel and a piston capable of sliding in the barrel and sealing the open end of the barrel opposite the nozzle, and further, said at least one component in step (a) includes one or more of the barrel, the tip seal and/or the piston. Most preferably, said at least one component in step (a) includes at least the barrel of the syringe. The present invention also provides a novel method for molding a syringe component, such as a barrel, tip seal or piston, comprising the step of molding said component under conditions which are substantially free of pyrogens and viable and non-viable particulates.

The method of the present invention, wherein at least one of the aforementioned components, preferably at least the barrel, is molded under conditions which are substantially free of pyrogens and viable and non-viable particulates, allows the preparation of a pre-filled plastic syringe in a less cumbersome and more efficient manner than known methods by obviating the need for subsequent treatment steps such as water washing. Thus, while the component(s) molded under conditions which are substantially free of pyrogens and viable and non-viable particulates may optionally be treated subsequent to molding, such as by water washing, such subsequent steps may be omitted or reduced in intensity or duration by use of the present method.

Preferably, the component(s) molded under conditions which are substantially free of pyrogens and viable and non-viable particulates in accordance with step (a) are maintained under clean conditions until they are assembled in the syringe. In this regard, it is further preferred that clean conditions be maintained at least until the syringe is completely assembled (for example, that the partly assembled syringe be maintained under clean conditions). Thus, in a preferred embodiment, the present invention provides a method for the preparation of a pre-filled plastic syringe, wherein said syringe comprises the aforementioned barrel, tip seal and piston, comprising the steps of:

(a)
  (i) providing a barrel which is molded under conditions which are substantially free of pyrogens and viable and non-viable particulates, and, optionally, providing a tip seal and/or a piston which is also molded under conditions which are substantially free of pyrogens and viable and non-viable particulates; and
  (ii) maintaining said barrel and, optionally, said tip seal and/or piston, under clean conditions for use in step (b); and (b) filling and assembling said syringe.

In a particularly preferred embodiment, the present invention provides a method for the preparation of a pre-filled plastic syringe, wherein said syringe comprises the aforementioned barrel, tip seal and piston, comprising the steps of:

(a)
  (i) providing a barrel which is molded under conditions which are substantially free of pyrogens and viable and non-viable particulates, and, optionally, providing a tip seal and/or a piston which is also molded under conditions which are substantially free of pyrogens and viable and non-viable particulates; and
  (ii) maintaining said barrel and, optionally, said tip seal and/or piston, under clean conditions for use in step (b); and (b) filling and assembling said syringe, wherein:
  (i) the tip seal is attached to the nozzle end of said barrel;
  (ii) the barrel and tip seal assembly is filled with a liquid or semi-solid through the open end of the barrel, said open end being opposite said nozzle end of the barrel; and
  (iii) the piston is assembled in said open end of the barrel; and (c) optionally, sterilizing the assembled syringe and its contents.

BRIEF DESCRIPTION OF THE DRAWINGS

FIG. 2 is a table defining the airborne particulate cleanliness classes in accordance with Federal Standard 209(E) of Sep. 11, 1992:

FIG. 3 shows three tables indicating classes of microbial levels under different conditions as set forth in Pharmacopeial Forum, Vol. 18, No. 55 pp. 4048–54 (Sept.–Oct. 1992).

DETAILED DESCRIPTION OF THE INVENTION

Figure 1:
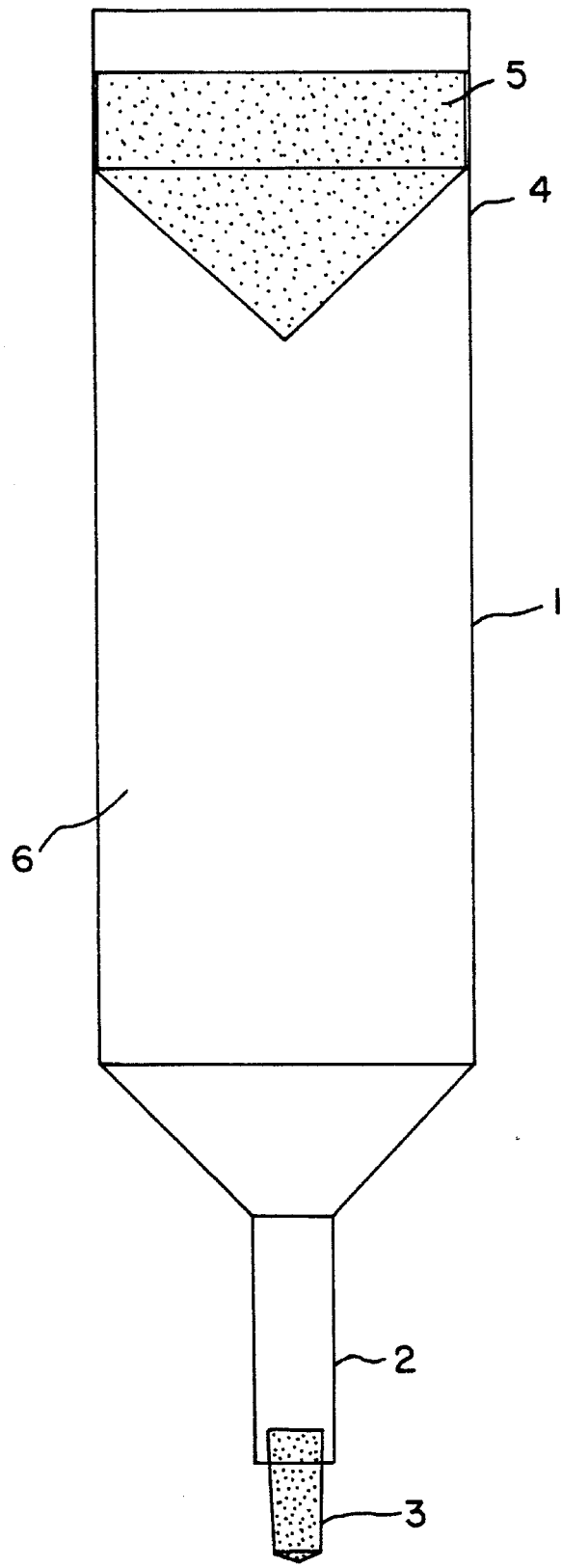
FIG. 1 is a sectional view of a pre-filled plastic syringe prepared by the present method.

A preferred configuration of a pre-filled plastic syringe prepared by the present method is illustrated in FIG. 1. As can be seen from FIG. 1, the barrel 1 has a nozzle end 2, to which is attached a tip seal 3 and, at the opposite end 4, a plunger (or piston) 5. The piston may be depressed to express the liquid or semi-solid contents 6 of the syringe through the nozzle end.

According to the present method, at least one syringe component, preferably at least the barrel, is molded under conditions which are substantially free of pyrogens and viable and non-viable particulates. The term "molded under conditions which are substantially free of pyrogens and viable and non-viable particulates", as used herein, denotes molding under conditions meeting or exceeding Class 100,000 conditions with respect to particulates (Federal Standard No. 209E, "Airborne Particulate Cleanliness Classes in Cleanrooms and Clean Zones, approved by the General Services Administration (Sept. 11, 1992); see FIG. 2, Table 1, and, with respect to microbes, meeting or exceeding Class MCB-3 conditions (Pharmacopeial Forum, Volume 18, Number 5, pp. 4048 to 4054, In-Process Revision, The United States Pharmacopeial Convention, Inc. (Sept.–Oct. 1992); see FIG. 3, Table 2, 3 and 4, and, in addition, wherein the microbial level of gram negative microorganisms is less than 1 cfu (colony forming unit) per cubic foot of air (and, preferably, also per 30 $cm^2$ of surface). Class MCB-3 conditions, and/or the aforementioned level of gram negative organisms, may be maintained, for example, by sampling to determine the level of microbes present, and sanitizing or employing other control methods as required (e.g., by surface contact with alcohol, phenolic germicides such as "germ warfare®", or chlorite salts such as sodium chlorite salts (e.g., "Exspore")). As is understood by one of ordinary skill in the art, "meeting or exceeding" denotes a level of cleanliness which is equal to or greater than the standard referred to.

With respect to particulates, the term "molded under conditions which are substantially free of pyrogens and viable and non-viable particulates", as used herein, preferably denotes molding under conditions meeting or exceeding Class 10,000 conditions (see FIG. 2 Table 1); more preferably, conditions meeting or exceeding Class 1,000 conditions (see FIG. 2 Table 1; and most preferably, under conditions meeting or exceeding Class 100 conditions (see FIG. 2, Table 1). With respect to microbes, the term "molded under conditions which are substantially free of pyrogens and viable and non-viable particulates", as used herein, preferably denotes molding under conditions meeting or exceeding Class MCB-2 conditions (see FIG. 3, Table 2, 3, and 4); and more preferably, conditions meeting or exceeding Class MCB-1 conditions (see FIG. 3, Table 2, 3, and 4).

In addition to conducting the molding step under conditions which are substantially free of pyrogens and viable and non-viable particulates (that is, under the classified conditions described above), it is preferred to employ an elevated temperature and/or pressure during molding, for example, a temperature and/or pressure where pyrogens, if present, may be partly or completely decomposed during molding. Also, if desired, the starting plastic material may be treated, for example, washed, such as with an aqueous (e.g., water for injection) or organic washing agent and/or sterilized, such as treated with ethylene oxide or irradiated, prior to molding.

Preferably, as indicated above, a component molded under conditions which are substantially free of pyrogens and viable and non-viable particulates is maintained under clean conditions prior to assembly into the syringe. "Clean conditions" include those defined above for conditions which are substantially free of pyrogens and viable and non-viable particulates, but may also include any art-recognized conditions for maintaining cleanliness such as enclosure in a sealed clean-room bag or wrapper for storage.

A syringe component molded under conditions according to step (a) of the method of the present invention may be provided which is substantially free of pyrogens and viable and non-viable particulates and which is suitable for assembly into a sterile syringe with minimal or no further treatment of the component prior to assembly. Thus, for example, a component such as the barrel molded under the conditions of step (a) of the present method may be assembled into the syringe without water washing. If desired, however, some further treatment may, optionally, be employed subsequent to molding.

In this regard, any of the components of the syringe, including those molded under the conditions of step (a) of the present method, as well as those molded under other conditions ("non-classified conditions"), may optionally be treated by one or more of the following steps subsequent to molding:

(1) blowing the component with a gas, especially with sterile filtered (e.g., filtered through a 0.2 μm filter) and/or deionized (facilitating a decrease in the electrostatic attraction of particles to the molded component) air to remove particulate matter;

(2) lubricating the component, such as by treatment with a silicone lubricant;

(3) washing the component with an inorganic (e.g., hydrogen peroxide or water) and/or organic (e.g., freon) washing agent, and, optionally, rinsing the component, such as with water;

(4) sterilizing the component, such as by contact with an antimicrobial agent (for example, hydrogen peroxide (e.g., in liquid or vapor form) or ethylene oxide), by use of radiation (especially, gamma radiation), and/or by autoclaving (such as by use of steam at temperatures of 122° to 124° C. and pressures of 33 to 35 psia); and/or (5) preparing the component for storage or transport, such as by placing the component in a sealed, clean-room bag where it is not to be employed immediately after formation.

For those components molded under conditions which do not meet the conditions of step (a) of the present method, for example, Class 100,000 conditions where microbial monitoring is not employed or other clean room-type conditions not meeting the conditions of step (a), it is preferred that, at a minimum, a washing step, such as the above step (3) be employed.

Preferred Methods for Preparation of Barrel

The barrel of the syringe may be made of any suitable plastic, and is preferably made of polyolefin, including polyolefin polymers, copolymers and blends, especially polypropylene or blends thereof with polyethylene, or olefin polymers and copolymers including methylpentene, or the like polyolefins.

Preferably, the barrel is injection molded, such as by use of injection molding equipment under conditions known in the art for melting and forming plastics (e.g., injection molding polypropylene pellets into syringe barrels by melting at 400° to 520° F. (0.75 to 3 minutes) at 1000 to 1200 psi).

Preferred Methods for Preparation of Tip Seals

The tip seal of the syringe may be made of any suitable plastic, and is preferably made of flexible rubber elastomer such as natural rubber, butyl or halobutyl rubber or blends thereof. The tip seal may be molded, preferably injection or compression molded, such as by use of injection or compression molding equipment under conditions known in the art. The equipment may, for example, be readily selected by one of ordinary skill in the art on the basis of the type of elastomer employed.

Preferred Methods for Preparation of Piston

The piston may be any suitable type, such as a piston operable by a rod or handle for hand injection of the contents of the syringe or a piston operable by a power injector for mechanical injection of the contents of the syringe.

The piston may be made of one, two or more pieces. The piston may, for example, be a single piece component, or a two-piece component consisting of a core and a flexible cover piece attached to or fitting over or onto the core (e.g., allowing the piston to seal the barrel of the syringe). In the latter case, the core is preferably made of a relatively hard plastic such as a polyolefin (e.g., polypropylene) or polycarbonate, and the flexible cover piece is preferably made of a flexible rubber elastomer, such as those materials described above with respect to the tip seal; the two pieces may be pre-assembled to form the piston prior to insertion into the barrel. Each of the separate pieces of the piston may be molded and optionally treated as described above.

Preferred Methods for Assembly of Syringe

In a preferred embodiment of the present method, the tip seal is assembled by attachment to the barrel, preferably automatically. Filling may then be conducted, such as by use of automatic filling equipment. The syringe may be filled with any suitable liquid (e.g., solution or suspension) or semi-solid (e.g., paste, cream or ointment). Preferably, the syringe is filled with a liquid diagnostic agent suitable for injection, for example, a contrast agent such as ProHance™ (gadoteridol) or Isovue® (iopamidol).

The liquid or semi-solid may then be sealed by insertion of the piston, optionally followed by a terminal sterilization step. When employed, sterilization is preferably achieved by steam autoclaving. Preferred temperatures for steam autoclaving are those from about 120° to 124° C.; preferred pressures are those from about 44 to 53 psia. It is particularly preferred to select a pressure set point so that, under the conditions of the autoclaving, the pressure inside the syringe is approximately in equilibrium with the pressure outside the syringe in the autoclave. An overpressure (pressure outside syringe in autoclave exceeds that in syringe) or an underpressure (pressure in syringe exceeds that outside syringe in autoclave) may, however, also be employed.

In addition to the tip seal, barrel and piston, the syringe prepared by the present invention may include other components, such as any of those known in the art, for example, a handle or rod for the piston, a needle, a protective cap for the needle, and the like.

The following Example further illustrates the present invention, and is not intended to in any way limit the scope of the present claims.

EXAMPLE 1

PREPARATION OF PRE-FILLED PLASTIC SYRINGES

In the following Example, wherever Class 100 conditions are employed, it is understood that the microbial level of gram negative microorganisms is less than 1 cfu (colony forming unit) per cubic foot of air or per 30 cm$^2$ of surface, and that the conditions meet or exceed Class MCB-3 conditions.

Preparation of Syringe Components (i) Barrels

Polypropylene resin pellets, prepared by extrusion of a molten (400° to 520° F.) polypropylene resin mix (suitable for formation of clear plastic barrels) into pellet form, are pneumatically loaded into a hopper and fed into a sprew under Class 100,000 conditions. The pellets are then melted at 400° to 520° F. for 0.75 to 3 minutes while under 1000 to 1200 psi (also under Class 100,000 conditions). (Methylpentene olefin resin pellets may alternatively be employed, and are preferably dried at 160° F. for 4 hours prior to being fed into the sprew.)

Under Class 100 conditions (for this and the following steps unless indicated otherwise), the syringe barrels are formed by injection molding of the molten resin, and the formed barrels are picked robotically from the mold. The barrels are optionally blown with 0.2 μm sterile filtered, deionized air and/or lubricated with silicone. The barrels are then presented by the robot for visual inspection. A Class 100 molded polycarbonate Luer nut may optionally be machine assembled at this time.

Still under Class 100 conditions, the barrels are matrixed (oriented) into a Class 100 molded polypropylene carrier holder, aligning the barrels for further processing. The barrels may optionally be placed in heat-sealed clean-room bags when stored prior to use. The barrels may also optionally be sterilized, such as by contact with ethylene oxide or by autoclaving. When gas sterilization is contemplated, it is preferred to place the barrels in gas permeable heat-sealed clean-room bags and to sterilize the barrels in situ.

(ii) Tip Seals

Halobutyl rubber is compression molded under Class 100,000 conditions to produce flexible rubber tip seals. Under Class 100 conditions, the tip seals are washed with purified water, United States Pharmacopeia, XXII (1990) (hereinafter, "U.S.P., XXII") which is treated to be pyrogen free or, preferably, water for injection, U.S.P., XXII, optionally siliconized, and optionally placed in heat-sealed clean-room bags when stored prior to use (gas permeable such bags may be employed when gas sterilization, such as by ethylene oxide or autoclaving, in situ is desired (see the "Assembly and Fill" section below); such bags may be other than gas permeable if it desired to employ a method of sterilization such as irradiation).

(iii) Pistons

Two-piece pistons are prepared by assembling, preferably mechanically, under Class 100 conditions, an inner hard plastic core and a flexible rubber cover. The pistons may optionally be placed in heat-sealed clean-room bags (preferably, gas permeable such bags when gas sterilization in situ is desired) when stored prior to use and/or sterilized, such as by gamma irradiation, or, preferably, by contact with ethylene oxide or by steam autoclaving.

Cores

The cores of the pistons are made from polypropylene (or, alternatively, polycarbonate) molded under the Class 100 conditions described above for molding the barrels. The cores may, alternatively, be molded under non-classified conditions and washed with water for injection U.S.P., XXII or purified water U.S.P., XXII which is treated to be pyrogen free. Optionally, the cores may be placed in heat-sealed clean-room bags (e.g., gas permeable for reasons described above) when stored prior to use.

Covers

The flexible rubber covers are molded under the conditions used to prepare the flexible rubber tip seals, and, under Class 100 conditions, are washed with water for injection U.S.P., XXII or purified water U.S.P., XXII which is treated to be pyrogen free, and siliconized. The flexible rubber covers may optionally be placed in heat-sealed clean-room bags (e.g., gas permeable for reasons described above) when stored prior to use.

Assembly and Fill

The tip seals are sterilized, such as by contact with ethylene oxide or by irradiation or, preferably, by steam autoclaving, and, under Class 100 conditions, are placed into the hopper of a filling machine, and assembled to the barrels. Also under Class 100 conditions, liquid contrast agent, such as Isovue® or ProHance™, is filled into the barrel through the open piston end.

The two-piece pre-assembled pistons, placed into the filling machine hopper, are inserted into the barrels using a vacuum seating mechanism. The filled syringes are steam autoclaved at a temperature between 120° and 124° C. and a pressure between 44 and 53 psia. Following particulate inspection, the syringes are labeled and packaged for use.

What is claimed is:

1. A method for the preparation of a pre-filled plastic syringe including a plurality of components, comprising the steps of:
   (a) providing at least one component of said syringe which is molded under conditions which are substantially free of pyrogens and viable and non-viable particulates, said conditions meeting a cleanliness level of about Class 100; and
   (b) filling and assembling said syringe.

2. The method of claim 1, wherein said syringe comprises as components a barrel, a tip seal capable of sealing the nozzle of the barrel and a piston capable of sliding in the barrel and sealing the open end of the barrel opposite the nozzle, and further, wherein said at least one component in step (a) includes one or more of said barrel, said tip seal and/or said piston.

3. The method of claim 2, wherein said at least one component of step (a) includes said barrel.

4. The method of claim 3, further comprising the step of: maintaining said barrel under clean conditions for use in step (b).

5. The method of claim 4, wherein step (a) further includes providing a tip seal or piston or both which are molded under conditions which are substantially free of pyrogens and viable and non-viable particulates, and maintaining all the components provided in step (a) under clean conditions for use in step (b).

6. The method of claim 4, wherein said step (b) comprises the steps of:
   (b)
   (i) attaching the tip seal to the nozzle end of said barrel;
   (ii) filling the barrel and tip seal assembly with a liquid or semi-solid through the open end of the barrel, said open end being opposite said nozzle end of the barrel; and
   (iii) assembling the piston in said open end of the barrel.

7. The method of claim 6, wherein following step (b) the assembled syringe and its contents are sterilized.

8. The method of claim 2, wherein said at least one component in step (a) is molded under conditions meeting or exceeding Class MCB-2 conditions.

9. The method of claim 8, wherein said at least one component in step (a) is molded under conditions meeting or exceeding Class MCB-1 conditions.

10. The method of claim 2, wherein said at least one component of said syringe is treated by one or more of the following steps subsequent to molding:
    (1) blowing the component with a gas;
    (2) lubricating the component;
    (3) washing the component with an inorganic or organic washing agent or both, and, optionally, rinsing the component;
    (4) sterilizing the component;
    (5) preparing the component for storage or transport.

11. The method of claim 10, wherein the component(s) of the syringe that are not molded under conditions which are substantially free of pyrogens and viable and non-viable particulates in accordance with step (a) are, prior to assembly into said syringe, sterilized or washed with an inorganic or organic washing agent and optionally rinsed, or, prior to assembly into said syringe, sterilized and washed with an inorganic or organic washing agent and optionally rinsed.

12. The method of claim 1, wherein said at least one component in step (a) is molded under conditions meeting or exceeding Class 100 conditions.

13. The method of claim 1, further comprising monitoring of microbial and non-viable particulate levels in the molding area to maintain said conditions which are substantially free of pyrogens and viable and non-viable particulates.

14. The method of claim 1, wherein said at least one component of said syringe is formed from plastic, and prior to molding the plastic is washed with an aqueous or organic washing agent or sterilized or both washed and sterilized.

15. A method for molding a syringe component, comprising the step of molding said component under conditions which are substantially free of pyrogens and viable and non-viable particulates, said conditions meeting a cleanliness level of about Class 100.

16. The method of claim 15, wherein said syringe component is a barrel, tip seal or piston.

* * * * *

(12) REEXAMINATION CERTIFICATE (4737th)

United States Patent
Heffernan et al.

(10) Number: US 5,620,425 C1
(45) Certificate Issued: Feb. 18, 2003

(54) METHOD FOR THE PREPARATION OF PRE-FILLED PLASTIC SYRINGES

(75) Inventors: Gayle Heffernan, Middlesex, NJ (US); Allen Welsher, East Brunswick, NJ (US)

(73) Assignee: Bracco International B.V., Amsterdam (NL)

Reexamination Request:
No. 90/004,870, Dec. 12, 1997
No. 90/005,344, Apr. 26, 1999

Reexamination Certificate for:
Patent No.: 5,620,425
Issued: Apr. 15, 1997
Appl. No.: 08/147,353
Filed: Nov. 3, 1993

(51) Int. Cl.⁷ ................................................. A61M 1/00
(52) U.S. Cl. ........................... 604/28; 141/11; 604/232; 604/187; 128/898
(58) Field of Search ................................. 604/218, 232, 604/265, 267, 199; 128/898; 141/11, 91; 422/27, 28, 100, 102, 302; 53/122

(56) References Cited

U.S. PATENT DOCUMENTS

| | | | |
|---|---|---|---|
| 3,634,997 A | 1/1972 | Tait | 53/127 |
| 4,718,463 A | 1/1988 | Jurgens, Jr. et al. | 141/11 |
| 4,880,581 A | 11/1989 | Dastoli et al. | |
| 5,141,430 A | 8/1992 | Maus et al. | |

FOREIGN PATENT DOCUMENTS

GB  877372  8/1961

OTHER PUBLICATIONS

"Clean–Room Injection Moulding", by H. Eckhardt, *Plast Europe*, (Mar. 1992).
"Disposable syringes: Klockner standards for mass production", *PSA* (Sep. 1991).
"Cleanroom Design", by W. Whyte, John Wiley & Sons, Ltd., (1991).
"Microbiological Evaluation And Classification Of Clean Rooms And Clean Zones", Pharamacopeial Forum, vol. 18, No. 5, (Sep.–Oct. 1992).

*Primary Examiner*—Anh-Tuan T. Nguyen

(57) ABSTRACT

A novel method for the preparation of a pre-filled plastic syringe, and preferably the preparation of a plastic syringe pre-filled with a diagnostic contrast agent, wherein said syringe comprises as components a barrel, a tip seal capable of sealing the nozzle of the barrel and a piston capable of sliding in the barrel and sealing the open end of the barrel opposite the nozzle, comprising the steps of (a) providing at least one component of said syringe which is molded under conditions which are substantially free of pyrogens and viable and non-viable particulates; and (b) filling and assembling said syringe.

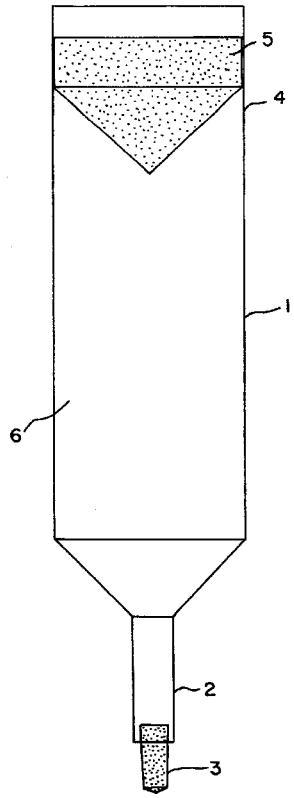

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 15 are determined to be patentable as amended.

Claims 2–14 and 16, dependent on an amended claim, are determined to be patentable.

1. A method for the preparation of a pre-filled plastic syringe including a plurality of components, comprising the steps of:

(a) [providing] *molding* at least one component of said syringe [which is molded] under conditions which are substantially free of pyrogens and viable and non-viable particulates, said conditions meeting, *with respect to particulates,* a cleanliness level of about Class 100 *and, with respect to microbes, meeting a cleanliness level of Class MCB-3 and meeting a microbial level of gram negative microorganisms of less than 1 colony forming unit (cfu) per cubic foot of air*; and (b) filling and assembling said syringe.

15. A method for molding a syringe component, comprising the step of molding said component under conditions which are substantially free of pyrogens and viable and non-viable particulates, said conditions meeting, *with respect to particulates,* a cleanliness level of about Class 100 *and, with respect to microbes, meeting a cleanliness level of Class MCB-3 and meeting a microbial level of gram negative microorganisms of less than 1 colony forming unit (cfu) per cubic foot of air.*

* * * * *